(12) United States Patent
Robinson

(10) Patent No.: US 10,718,748 B2
(45) Date of Patent: Jul. 21, 2020

(54) GAS ANALYSIS

(71) Applicant: General Electric Technology GmbH, Baden (CH)

(72) Inventor: David Peter Robinson, Lisburn (GB)

(73) Assignee: General Electric Technology GmbH, Baden (CH)

( * ) Notice: Subject to any disclaimer, the term of this patent is extended or adjusted under 35 U.S.C. 154(b) by 0 days.

(21) Appl. No.: 15/832,451

(22) Filed: Dec. 5, 2017

(65) Prior Publication Data
US 2018/0180588 A1      Jun. 28, 2018

(30) Foreign Application Priority Data

Dec. 22, 2016  (EP) ..................................... 16206168

(51) Int. Cl.
| | | |
|---|---|---|
| G01N 33/28 | (2006.01) | |
| G01N 21/03 | (2006.01) | |
| G01N 21/84 | (2006.01) | |
| G01R 31/50 | (2020.01) | |

(52) U.S. Cl.
CPC ....... G01N 33/2841 (2013.01); G01N 21/031 (2013.01); G01N 21/0303 (2013.01); G01N 21/84 (2013.01); *G01N 2021/036* (2013.01); *G01N 2201/0227* (2013.01); *G01N 2201/066* (2013.01); *G01N 2201/1241* (2013.01); *G01R 31/50* (2020.01)

(58) Field of Classification Search
CPC ....... G01N 2291/0255; G01N 33/2841; G01N 21/84; G01R 31/02
USPC ... 73/19.1, 23.2, 28.01, 31.01, 31.02, 31.03, 73/31.05, 432.1
See application file for complete search history.

(56) References Cited

U.S. PATENT DOCUMENTS

| | | | | |
|---|---|---|---|---|
| 3,704,955 A | * | 12/1972 | Siegler, Jr. ............. | G01N 21/65 356/244 |
| 4,209,232 A | * | 6/1980 | Chernin ............... | G01N 21/031 356/246 |
| 5,039,224 A | * | 8/1991 | O'Rourke .......... | G01N 21/0303 356/434 |

(Continued)

FOREIGN PATENT DOCUMENTS

| | | |
|---|---|---|
| WO | 97/49983 A1 | 12/1997 |
| WO | 2015/183298 A1 | 12/2015 |

OTHER PUBLICATIONS

Altmann, J., et al., "Two-mirror multipass absorption cell," Applied Optics, vol. 20, No. 6, pp. 995-999 (Mar. 15, 1981).

(Continued)

*Primary Examiner* — Suman K Nath
(74) *Attorney, Agent, or Firm* — Eversheds Sutherland (US) LLP

(57) ABSTRACT

An apparatus may have a first reflector and a second reflector positioned on either side of a sample volume for a gas sample. The configuration of the first reflector may be variable between at least first and second configurations, wherein each of the first and second configurations is arranged such that a beam of optical radiation from an optical beam origin is directed to a detector location via the sample volume. In the second configuration the beam of optical radiation is reflected at least once from each of the first and second reflectors and the path length of the beam of optical radiation through the sample volume is greater than in the first configuration.

14 Claims, 2 Drawing Sheets

(56) References Cited

U.S. PATENT DOCUMENTS

| | | |
|---|---|---|
| 2006/0158644 A1 | 7/2006 | Silver |
| 2010/0238446 A1 | 9/2010 | Akiyama et al. |
| 2013/0003045 A1 | 1/2013 | Wilkins |
| 2015/0097551 A1 | 4/2015 | Yao |
| 2016/0054286 A1 | 2/2016 | Van Mechelen et al. |

OTHER PUBLICATIONS

Extended European Search Report and Opinion issued in connection with corresponding EP Application No. 16206168.3 dated Apr. 24, 2017.

* cited by examiner

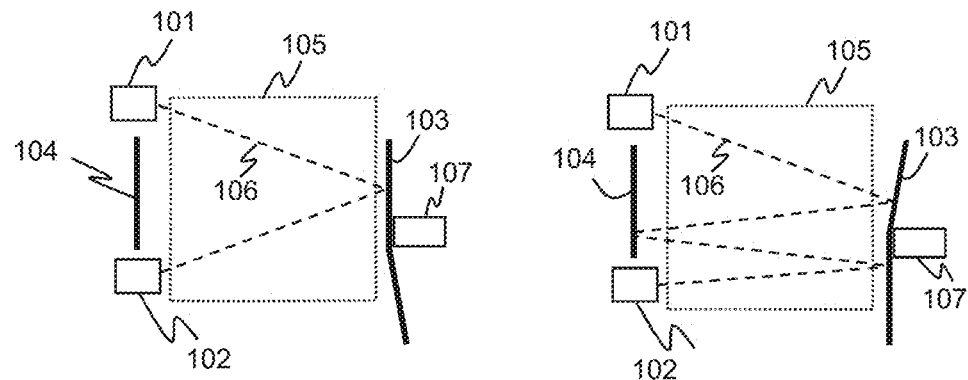
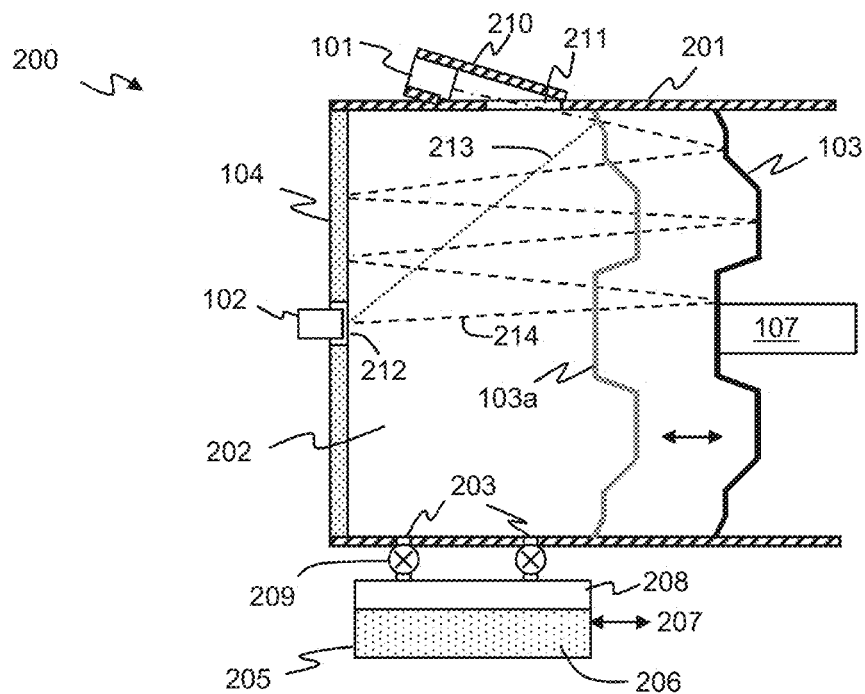
Figure 1
Figure 2

GAS ANALYSIS

BACKGROUND OF THE INVENTION

Embodiments of the invention relate to methods and apparatus for trace gas analysis, in particular to optical gas analysis, and especially to detection of target species indicative of breakdown of insulating oil.

Gas analysis, where a sample may be analysed to determine the presence of one or more target species of gas, is useful in a range of applications.

One particular application is for monitoring of electrical components, such as transformers, in a high voltage electrical power generation or distribution system. Large scale electrical transformers may be used in various power generation or distribution systems. Various parts of the transformer need to be electrically insulated from other parts of the transformer and/or the surrounding environment and it is typical that at least part of the insulation is provided by an insulating oil. Insulating oil may for instance be provided within a housing to cool and insulate the transformer windings.

The insulating oil is chosen to have suitable properties for the expected normal operating conditions. However if an electrical fault develops this could result in abnormal operating conditions. For instance in the event of some electrical faults there may be significant localised heating of the insulating oil, above what may normally be expected, and/or an electrical discharge within the insulating oil. Such electrical faults can result in breakdown of the components of the insulating oil and generate decomposition gases dissolved within the oil.

Suitable insulating oils, such as mineral oil, generally contain long chain hydrocarbon molecules. Electrical faults may result in breakdown of the insulating oil into various different components, such as acetylene, ethane or ethylene for example. These decomposition components may be produced as gases dissolved in the insulating oil and may only be present if the insulating oil has been subjected to some abnormal operating condition. Detecting the presence of such decomposition gases thus provides useful information about the occurrence of electrical faults, which is useful as part of a monitoring system, for example for preventative maintenance.

Dissolved gas analysis is a known technique where a sample of the insulating oil may be tapped from the transformer and tested for the presence of any decomposition gases of interest. Detecting the presence of decomposition gases may be indicative of a fault and the type of decomposition gas, concentration and rate of change may provide information about the type and/or severity of the fault. Such dissolved gas analysis does typically however require oil to be removed from the transformer and often requires the oil to be sent to a dedicated testing laboratory.

SUMMARY OF INVENTION

Embodiments of the present disclosure relate to methods and apparatus for gas analysis, especially for detecting trace amounts of gas in a sample, for example for detecting target species corresponding to decomposition gases of insulating oil.

Thus according to a first aspect there is provided an apparatus for gas analysis comprising: a first reflector and a second reflector positioned on either side of a sample volume for a gas sample; wherein the configuration of the first reflector is variable between at least first and second configurations; wherein each of the first and second configurations is arranged such that a beam of optical radiation from an optical beam origin is directed to a detector location via the sample volume; and wherein in the second configuration the beam of optical radiation is reflected at least once from each of the first and second reflectors and the path length of the beam of optical radiation through the sample volume is greater than in the first configuration.

By varying the configuration of the first reflector between the first and second configurations the path length of the beam of optical radiation through the sample volume can be varied. This will vary to the extent to which target species of interest in the gas in the sample volume will interact with the beam of optical radiation and hence vary the sensitivity of the gas analysis. As will be explained in more detail below the path length may vary to a different number of passes through the sample volume.

The apparatus may comprise a housing, with the first reflector and the second reflector located within the housing. The apparatus may further comprise an actuator for moving the first reflector to a first position within the housing to provide the first configuration and to a second position within the housing to provide the first configuration. In some embodiments the second position of the first reflector has a greater separation from the second reflector than the first position. In other words moving from the first position to the second position increases the separation between the first and second reflectors.

In some embodiments the first reflector is mounted on or forms part of a wall of a sample chamber for the gas to be analysed, such that movement of the first reflector from the first position to the second position results in an increase in volume of the sample chamber. If the sample chamber is sealed, in use, this can reduce the pressure within the sample chamber.

The position of the optical beam origin and/or the detector location may be fixed with respect to the housing. In some embodiments the position of the second reflector is fixed with respect to the housing. Thus the first and second configurations may be provided just by the first reflector moving within the housing.

At least one of the first reflector and the second reflector may have a non-planar reflective surface such that in the first configuration the beam of optical radiation is incident on at least one of the first reflector and the second reflector with a different angle of incidence to the second configuration.

In one embodiment the first configuration corresponds to one or more passes of the beam of optical radiation through the sample volume and the second configuration corresponds to three or more passes of the beam of optical radiation through the sample volume.

The optical beam origin may comprise a mount for locating an optical source. An optical source may be located at the optical beam origin. A photodetector may be located at the detector location. In some implementations the detector location is located at the centre of the second reflector.

In another aspect there is provided a method of gas analysis comprising: introducing a gas to be analysed into a sample volume located between a first reflector and a second reflector; directing a beam of optical radiation from an optical source to a photodetector via the sample volume with the first reflector at a first configuration; and directing a beam of optical radiation from an optical source to a photodetector via the sample volume with the first reflector at a second configuration; wherein in the second configuration the beam of optical radiation is reflected at least once from each of the first and second reflectors and the path length of the beam of optical radiation through the sample volume is greater than in the first configuration.

The method may involve moving the first reflector further away from the second reflector to move from the first configuration to the second configuration and also to reduce the pressure of the gas within the sample volume.

The method may further comprise moving the first reflector with respect to the second reflector and monitoring the intensity at the photodetector to determine an optimal position for at least one of the first and second configurations.

The method may be implemented using the apparatus of any of the variants discussed.

BRIEF DESCRIPTION OF THE DRAWINGS

Various aspects of the present disclosure will now be described, by way of example only, with reference to the accompanying figures, of which:

FIG. 1 illustrates a gas analyser apparatus according to an embodiment;

FIG. 2 illustrates a gas analyser apparatus according to another embodiment.

DETAILED DESCRIPTION

Figure 3:
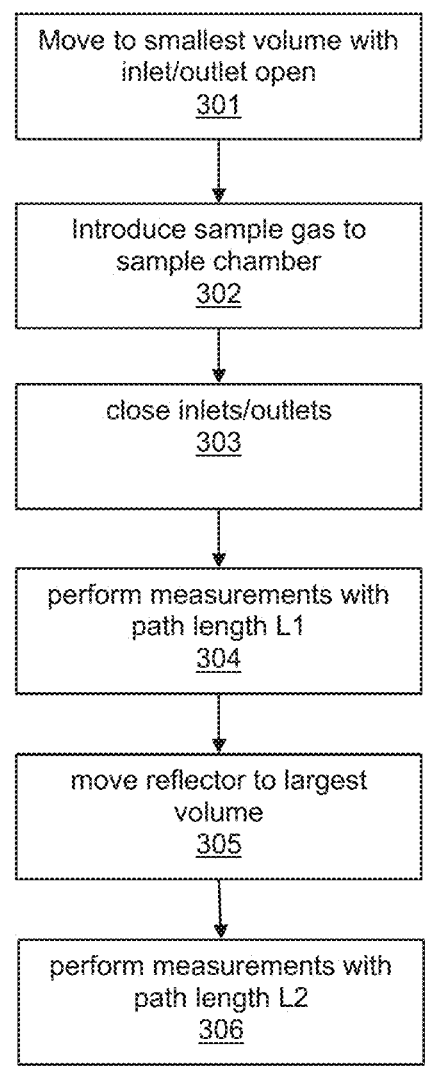
FIG. 3 illustrates a flow chart of a method of operation.

Embodiments of the present disclosure relate to gas analysis and especially to optical gas analysis. Optical gas analysis is a known technique in which a beam of optical radiation from an optical source is passed through a sample volume containing the gas to be analysed before being incident on a photodetector. The beam of optical radiation is chosen to comprise at least one wavelength which is known to interact with a target species, for instance to include a wavelength that may be relatively strongly absorbed or scattered by a target species. The optical radiation detected by the photodetector is analysed at the wavelength of interest. If the target species is present in the sample of gas then the intensity of optical radiation detected at the wavelength of interest may be lower than would be the case if the target species was absent. Comparing the detected intensity of radiation at the wavelength of interest to a known calibrated intensity and/or an intensity for a wavelength of the beam of optical radiation which does not interact with a target species can be used as an indicator of the presence of the target species and the relative intensity detected may provide an indication of the concentration of the gas sample in the species.

The properties of the optical source for generating the beam of optical radiation and the photodetector and their arrangement relative to one another and the sample volume is chosen to provide a certain sensitivity and detection range. Such gas analysers may usefully be employed in trace gas analysis.

Embodiments of the present disclosure relate to optical gas analysis with an improved sensitivity range, i.e. a wider range of sensitivity to different concentrations of the target species in the gas sample. Embodiments of the present disclosure vary the sensitivity range of the gas analyser by varying the optical path length for the beam of optical radiation within the sample volume. Varying the path length for the beam of optical radiation within the sample volume can effectively vary the amount of interaction between the beam and the sample gas before reaching the detector. For a given concentration of the target species, varying the path length within the sample volume will thus vary the amount of absorption experienced before the beam of optical radiation reaches the photodetector.

For example consider that the gas analyser is arranged to indicate that a target species is present in the gas sample if the intensity detected at the photodetector for the wavelength of interest drops below a defined threshold. If the path length through the sample volume is a first length then there may be a minimum concentration of the target species that will cause enough scattering/absorption to reduce the intensity reaching the photodetector to below the defined threshold. Thus there may be a minimum concentration level that can be reliably identified. Increasing the path length through the gas sample significantly may allow greater opportunity for the target species to interact with the optical beam and thus a longer path length through the sample volume may allow a lower concentration of the target species to be detected.

A variation in optical path length could be achieved by arranging the optical source to direct the beam of optical radiation on an optical axis that passes through the sample volume directly to the photodetector and by moving the photodetector within respect to the optical source along the optical axis. However this would require a significant degree of movement for an appreciable change in path length.

In embodiments of the present invention the optical path length may be varied by varying the number of passes of the beam of optical radiation through the sample volume. First and second reflectors are arranged on opposite sides of the sample volume and the first reflector is moveable between at least first and second configurations. In each configuration a beam of optical radiation from an origin location will be directed to a photodetector via the sample volume. In the second configuration the beam of optical radiation is reflected at least once from each of the first and second reflectors and the path length of the beam of radiation through the sample volume is greater than in the first configuration, due to a greater number of passes through the sample volume.

FIG. 1 illustrates the principles of an embodiment. FIG. 1 illustrates an optical source 101 arranged with respect to a photodetector 102 and a first reflector 103 and second reflector 104 on either side of a sample volume 105. In use the gas to be analysed is introduced into the sample volume 105 and the optical source 101 is activated to generate a beam of optical radiation 106. The left-hand side of FIG. 1 illustrates the first reflector 103 in a first configuration. In this configuration the beam of optical radiation 106 is incident on the reflector 103 and is reflected directly to the photodetector 102. Thus in this first configuration the beam of optical radiation passes twice through the sample volume 105. The right-hand side of FIG. 1 illustrates a second configuration. In this configuration the beam of optical radiation is incident on the first reflector 103 but in this configuration, instead of being reflected directly to the photodetector 102 is reflected toward the second reflector 104, where it is reflected back to the first reflector 103 and only then to the photodetector 102. Thus in the second configuration the beam of optical radiation has four passes through the sample volume 105. The path length for the beam of optical radiation 106 within the sample volume 105 in the second configuration is thus substantially twice that of the first configuration.

The first reflector may be moved between the first and second configurations by an actuator 107. It will be appreciated that to provide the different number of passes the angle of incidence of the beam of optical radiation 106 at the relevant part of the first reflector 103 is different in the first and second configurations. There are various ways in which this could be achieved. For instance the first reflector 103 could be rotated so that a different part of the first reflector is located in the path of the beam of optical radiation 106 in each of the first and second configurations. Additionally or alternatively at least part of the first reflector 103 could be tilted to a different angle in the first and second configurations.

In some embodiments the first and second configurations for the first reflector could be achieved by displacing the first reflector. FIG. 2 illustrates an apparatus 200 according to such an embodiment. FIG. 2 illustrates a housing 201 that at least partly defines a sealed sample chamber 202. A least one fluid passageway 203 may provide an inlet/outlet to the sample chamber 202 for the gas to be analysed. In some embodiments the fluid passageway(s) 203 may provide fluid communication to a reservoir 205 which contains the gas to be analysed.

In applications to analysis of insulating oil, the reservoir 205 could be a reservoir in which a sample of insulating oil 206 is held. The insulating oil could for instance be tapped from a transformer via a transfer arrangement 207 and/or the reservoir 205 may be part of a transformer. The insulating oil in the reservoir 205 may be allowed to settle and/or processed in some way so that any dissolved gases in the insulating oil 206 outgas into a headspace volume 208. A valve 209 associated with each fluid passageway 203 may be opened to allow the gas in the headspace area to fill the sample chamber 202. The valve(s) 209 may then be closed during the gas analysis.

In some instances the housing 201 may have a mount 210 for mounting, i.e. locating an optical source 101. The optical source 101 may, for instance, be a diode laser or the like and may produce a relatively narrow linewidth beam of optical radiation, in particular a beam of infrared radiation with a wavelength tuned to a particular target species of interest. Note as used herein the term optical radiation shall not be restricted to just the visible part of the electromagnetic spectrum and the term optical shall be taken to include infrared and ultraviolet radiation. Infrared radiation may be of particular interest for the target species of interest, such as acetylene. The optical source 101 may include optical components for focussing or collimating the beam of optical radiation so as to produce a relatively tightly focussed beam of optical radiation. The mount 210 may be configured to ease the location and alignment of the optical source 101. The mount 210 may hold the optical source within the sealed part of the housing 201, i.e. to form part of the sample chamber 202, or the optical source may be arranged to be coupled to the housing 201 to form a seal. In other embodiments the optical source could be arranged to direct the beam of optical radiation into the sample chamber 202 via a window portion 211 of the housing 201.

In this embodiment the beam of optical radiation is directed towards a moveable first reflector 103. The first reflector 103 is located on one side of the sample volume within sample chamber 202 and opposes a second reflector 104 on the other side of the sample chamber 202. It should be understood however that the optical source 101 may be arranged to initially direct the beam of optical radiation towards the second reflector 104.

The first reflector is moveable between at least a first position, i.e. arranged in first configuration, and a second position, i.e. arranged in second configuration. FIG. 2 illustrates the first reflector 103 in the second position, with the first position being illustrated by the grey outline 103a.

At the first position the incident beam may travel through at least part of the sample volume and be reflected from the first position of first reflector 103 towards the photodetector 102. In this embodiment the photodetector 102 may be located within or on one side of detector port 212 in the second reflector 104. The detector port 212 may ease location and/or alignment of the photodetector 102 within the apparatus 200. Again it will be understood however that the configuration illustrated in FIG. 2 is one example only and various arrangements of the optical source 101 and photodetector 102 may be used in different embodiments.

In the embodiment illustrated in FIG. 2 the beam of optical radiation may be directed directly from the first reflector (in the first position 103a) to the photodetector 102, as illustrated by the dotted line 213. Thus there are two passes of the beam of optical radiation through the sample volume, where a pass represents the free space travel of the beam of optical radiation between components of the apparatus 200. This will provide a first optical path length L1 through the sample volume.

In the second position of the first reflector 103 the beam of optical radiation is incident on a different part of the first reflector 103 and has a locally different angle of incidence to the surface of the first reflector 103. The beam of optical radiation is thus reflected in a different direction away from the first reflector 103 and, in this embodiment, travels on the path illustrated by dashed line 214. In this example the beam of optical radiation is reflected back and forth between the second reflector 104 and the first reflector 103 to provide six passes through the sample volume of sample chamber 202. This provides a significantly longer path length L2 through the sample volume than for the first position.

In one design similar to that illustrated in FIG. 2 the optical path length L1 through the sample chamber in the first position was of the order of 30 mm whereas the optical path length L2 through the sample chamber in the second position was of the order of 105 mm, with a linear movement of the first reflector of around 7 mm. Thus a relatively small linear movement of the first reflector can provide a significant increase in path length through the sample volume, for instance of the order of three times or greater.

The first reflector 103 may be moved between the first and second positions by a linear actuator 107. As noted above the extent of the linear movement need not be particularly large to achieve a significant variation in path length and hence a significant variation in the amount of interaction with the gas sample and hence sensitivity of the detector.

It will be noted that in the embodiment illustrated in FIG. 2 that in the first position the first reflector 103 is located closer to the second reflector 104 than in the second position. Thus the first and second reflectors 103 and 104 are configured with respect to one another such that increasing the separation between the reflectors may increase the number of passes through the sample volume and also the optical path length of an individual pass.

FIG. 2 illustrates that the first reflector 103, which is movable within the housing, has a varying surface profile, that is it has a non-flat or non-planar surface and the second reflector 104, which is fixed in relation to the housing has a general flat surface. It will be understood however that the first moveable reflector 103 could be planar and the second fixed reflector 104 could have the profiled surface or both reflector 103 and 104 could have appropriately profiled surfaces to provide the desired optical paths at the various positions.

The surface profile of the first reflector 103 and second reflector 104 are collectively configured to provide the different optical paths between the optical source 101 and the photodetector 102 in the first and second configurations. In each case the beam of optical radiation will be incident on either a different part of the first reflector 103 or the second reflector 104 and/or with a different angle of incidence to that part of the reflector.

FIG. 2 illustrates that the second reflector 104 is fixed with respect to the housing 201. This is a convenient implementation as providing only one moving reflector 103 is relatively simple, however in some implementations both of the first and second reflectors may be moveable with respect to the housing.

Additionally or alternatively in some implementations the position of least one of the optical source 101 and the photodetector 102 may be movable within the housing so as to alter the optical path length between the optical source 101 and the photodetector 102 within the sample chamber 202. Varying the position of the optical source 101 in this way can result in the beam of optical radiation being incident on a different part of the first reflector 103 and/or second reflector 104, and thus being reflected in a different direction to provide a different number of passes through the sample chamber 202. Moving the position of the photodetector 102 could change the position at which the photodetector 102 intercepts the beam of optical radiation and thus alter the number of passes through the sample chamber 202.

However moving the optical source 101 and/or the photodetector 102 may introduce issues with maintaining alignment and thus it may be preferred to keep the optical source 101 and the photodetector 102 in a fixed location within the housing 201 and just move the position of one of the reflectors 103 or 104.

The first and second positions of the first reflector 103 are known based on the design of the gas sensor, i.e. the relative positions of the optical source 101 and photodetector 102 and the surface profiles of the first and second reflectors 103 and 104. In practice however the alignment of the optical source 101 and/or positioning of the reflectors 103 and 104 may be slightly different from the design specification and/or may change due to the operating conditions, e.g. temperature. In some embodiments the actual position for the first reflector in the first and second configuration may be determined in a calibration step. The first reflector 103 could be located in or near a position expected to correspond to the first or second position. The optical source 101 and photodetector 102 may be active and the actuator 107 may adjust the position of the first reflector. Intensity readings could be taken from a variety of positions around the expected first or second position to determine the location of the first reflector that corresponds to the highest detected intensity and that location could be used as the relevant first or second configuration.

It should be noted that whilst FIG. 2 has been discussed with respect to a purely linear displacement of the first reflector 103 this could be combined with a rotation or tilting of part of the first reflector 103 and/or the second reflector 104.

The embodiment of FIG. 2 illustrates the optical source mounted at the rim of the housing 201 but it should be understood that the optical source may be located at any convenient position. An optical source positioned at the rim as illustrated in FIG. 2, with a centrally mounted detector would however allow the use of multiple optical sources (not illustrated in FIG. 2 for clarity). The position of the optical source 102 and the photodetector 101 may be varied in other embodiments to any convenient relative locations.

In each of the first and second configurations, e.g. the first and second positions of the reflector, it will be noted that the beam of optical radiation is only expected to be incident at part of the surface of the reflectors 103 and 104. The reflectors 103 and 104 thus need not be continuously reflective over their entire surface and may be reflective only in those parts where the beam of optical radiation will be incident in use.

As mentioned above in some instances the optical radiation may be chosen to have a relatively narrow wavelength range, e.g. to be a narrow line width beam of radiation at the wavelength of interest. A narrow linewidth may be useful to provide good sensitivity for the target species of interest.

However optical gas sensors can, in some instances, suffer from the effects of atmospheric broadening or pressure broadening. Pressure broadening is a known effect where the presence of other gas molecules interferes with the absorption or emission of radiation at a specific frequency, resulting in an effective spectral spreading in frequency. This can cause issues in gas analysis, especially at low concentrations of the target species, as an apparent drop in intensity at the photodetector may be due to pressure broadening rather than the presence of the target species.

To reduce the impact of pressure broadening some gas analysers may be provided with an evacuation pump to at least partly evacuate the sample chamber and reduce the pressure within the chamber whilst the analysis is being performed. This does however require the presence of a pump which may add to the cost and complexity of the apparatus.

In embodiments of the present disclosure, a linear movement of one of the reflectors may be used to cause a volume change in the sample chamber 202, after the sample chamber has been sealed, so as to effect a pressure change within the sample chamber 202, e.g. to reduce the pressure with the sample chamber.

Thus, referring back to FIG. 2, the first reflector 103 may be formed as part of or attached to a moveable end wall of the sample chamber 202, i.e. the first reflector 103 may form a seal with the edges of the housing 201 or be mounted on a moveable wall that does form such a seal. In use the first reflector 103 may be moved to vary both the optical path length of the beam of optical radiation within the sample chamber but also to vary the pressure within the sample chamber.

FIG. 3 illustrates a flowchart setting out one example method. At step 301 the first reflector may be moved to the first position, i.e. closest to the second reflector 104, to define the smallest volume of the sample chamber 202. The valve(s) 209 of the flow passageway(s) 203 are open to allow gas to escape. The gas of interest may then be introduced, at step 302, into sample chamber 202. The valves 209 of the flow passageway(s) 203 may simply be left open for long enough for the gas of interest to fill the sample chamber 202 or in some embodiments some flow stimulation may be used. The sample chamber 202 may thus be filled with the gas to be analysed at the pressure of the gas in the reservoir 205, which may for instance be atmospheric pressure. The valve(s) are then closed, at step 303, to seal the sample chamber. The optical source 101 and photodetector 102 may then be activated to perform, at step 304, a detection for the target species of interest. With the first reflector 103 in the first position the path length through the sample chamber is the path length L1, which is the short path length. This effectively provides the highest detection limit, i.e. the concentration of the target species required to provide a certain detectable drop in intensity is the greatest.

Thus if there is a high concentration of the target species present the target species will be detected and drop in intensity will reveal information about the concentration of the target species in a first range.

The method may then progress to step 305 where the first reflector 103 is moved by actuator 107 to the second position. In some instances this step may always be performed as part of the method but in other implementations the part of the method may be performed only if there was a negative detection at the first sensing step 304.

Moving the first reflector 103 to the second position increased the volume within the sample chamber 202. With valve(s) 209 closed the sample chamber is sealed and thus the increase in volume results in a reduction in pressure. The reduced pressure lessens the effect of pressure broadening and thus means that the gas analysis measurement, at step 306, is more accurate. The increased path length, L2, means that there is more opportunity for interaction between the target species and the beam of optical radiation, thus providing a more sensitive measurement. It will be appreciated that the reduced pressure does mean that the interaction of the target species per unit length of the beam path is also reduced but the path length L2 may, as described above, be significantly greater than the path length L1 and thus more than compensate for the reduce interaction rate. Thus in this second position the sensitivity of the gas analyser to concentrations of the target species is increased and a lower detection limit is achieved, with better accuracy due to the reduced pressure broadening.

The system detailed can also use the detector output to overcome mis-alignment of the first & second reflectors, by incremental movement of the second reflector, until an optimal signal is reached.

Embodiments of the present disclosure thus allow the path length of the beam of optical radiation through a sample volume to be increased at the same time that pressure within the sample volume is reduced. The path length variation and reduction in pressure can both be achieved through the movement of an element of the gas analysis apparatus, for instance a moveable reflector or a wall on which a moveable reflector is mounted. This avoids the need for a separate vacuum pump.

The embodiments described above have been described with respect to two different configurations each having a different optical path length through the sample volume due to a variation in the number of passes of the beam of optical radiation through the sample volume, and optionally with a consequent change in volume of the sample volume. In other embodiments however there may be at least one additional configuration top provide different path lengths through the sample volume and/or different sample volumes.

Embodiments are particularly useful for trace gas analysis for detecting decomposition gases from an insulating oil but in general the principles are applicable to any type of trace gas analysis.

It will be understood that the embodiments described above are given by way of example only and feature features and configurations may be changed. Unless otherwise explicitly ruled out by the context and of the features described with respect to one embodiment may be used, individual or in combination, in any of the other embodiments.

What is claimed is:

1. An apparatus for gas analysis comprising:
   a first reflector adjustably positioned on a first side of a sample chamber for a gas sample and a second reflector positioned on a second side of the sample chamber, the first reflector having a non-flat surface profile and the second reflector having a flat surface profile;
   wherein the first reflector is configured to change position from a first position in a first configuration to a second position in a second configuration;
   wherein the first reflector forms a wall of the sample chamber such that movement of the first reflector from the first position to the second position results in an increase in volume of the sample chamber and in a decreasing in pressure within the sample chamber to reduce the impact of pressure broadening;
   wherein each of the first configuration and the second configurations is arranged such that a beam of optical radiation from an optical beam origin is directed to a detector via the sample chamber; and
   wherein in the second configuration the beam of optical radiation is reflected at least once from each of the first and second reflectors and a path length of the beam of optical radiation through the sample chamber is greater than in the first configuration.

2. The apparatus as claimed in claim 1, wherein the apparatus comprises a housing, wherein the first reflector and the second reflector are located within the housing.

3. The apparatus as claimed in claim 2, comprising an actuator for moving the first reflector to a first position within the housing to provide the first configuration and to a second position within the housing to provide the second configuration.

4. The apparatus as claimed in claim 3, wherein the second position of the first reflector has a greater separation from the second reflector than the first position.

5. The apparatus as claimed in claim 2, wherein the position of the optical beam origin and the detector are fixed with respect to the housing.

6. The apparatus as claimed in claim 2, wherein the position of the second reflector is fixed with respect to the housing.

7. The apparatus as claimed in claim 1, wherein at least one of the first reflector and the second reflector have a non-planar reflective surface such that in the first configuration the beam of optical radiation is incident on at least one of the first reflector and the second reflector with a different angle of incidence to the second configuration.

8. The apparatus as claimed in claim 1, wherein the first configuration corresponds to one or more passes of the beam of optical radiation through the sample chamber and the second configuration corresponds to three or more passes of the beam of optical radiation through the sample chamber.

9. The apparatus as claimed in claim 1, wherein the optical beam origin comprises a mount for locating an optical source.

10. The apparatus as claimed in claim 1, further comprising an optical source located at the optical beam origin and wherein the detector is a photodetector.

11. The apparatus as claimed in claim 1, wherein the detector is located at the center of the second reflector.

12. A method, comprising:
    introducing a gas to be analysed into a sample chamber comprising a first reflector adjustably positioned on a first side of the sample chamber and a second reflector positioned on a second side of the sample chamber, the first reflector having a non-flat surface profile and the second reflector having a flat surface profile;
    directing a beam of optical radiation from an optical source to a photodetector via the sample chamber with the first reflector at a first configuration; and directing a beam of optical radiation from an optical source to a photodetector via the sample chamber with the first reflector at a second configuration;

wherein the first reflector forms a wall of the sample chamber such that movement of the first reflector from the first configuration to the second configuration results in an increase in volume of the sample chamber and in a decreasing in pressure within the sample chamber to reduce the impact of pressure broadening; and wherein in the second configuration the beam of optical radiation is reflected at least once from each of the first and second reflectors and a path length of the beam of radiation through the sample chamber is greater than in the first configuration.

13. The method as claimed in claim 12, wherein the method comprises moving the first reflector further away from the second reflector to move from the first configuration to the second configuration and also to reduce a pressure of the gas within the sample chamber.

14. The method as claimed in claim 13, further comprising moving the first reflector with respect to the second reflector and monitoring an intensity at the photodetector to determine an optimal position for at least one of the first and second configurations.

* * * * *